United States Patent
Hu

(10) Patent No.: US 10,111,587 B2
(45) Date of Patent: Oct. 30, 2018

(54) EYE MOTION SENSING METHOD, FLEXIBLE CONTACT BODY, EXTERNAL SENSING COIL AND SYSTEM

(71) Applicant: Kun Hu, Guangdong (CN)

(72) Inventor: Kun Hu, Guangdong (CN)

(73) Assignee: Shenzhen Zhiying Technologies Co., Ltd., Shenzhen (CN)

(*) Notice: Subject to any disclaimer, the term of this patent is extended or adjusted under 35 U.S.C. 154(b) by 130 days.

(21) Appl. No.: 15/095,222

(22) Filed: Apr. 11, 2016

(65) Prior Publication Data

US 2016/0278634 A1 Sep. 29, 2016

Related U.S. Application Data

(63) Continuation of application No. PCT/CN2014/088183, filed on Oct. 9, 2014.

(30) Foreign Application Priority Data

Oct. 10, 2013 (CN) .......................... 2013 1 0492430

(51) Int. Cl.
*A61B 3/14* (2006.01)
*A61B 3/113* (2006.01)
(Continued)

(52) U.S. Cl.
CPC ............ *A61B 3/113* (2013.01); *A61B 3/0025* (2013.01); *A61B 5/1103* (2013.01);
(Continued)

(58) Field of Classification Search
CPC ....... A61B 3/113; A61B 3/0025; A61B 5/162; A61B 5/1103; A61B 5/1126;
(Continued)

(56) References Cited

U.S. PATENT DOCUMENTS

| 2003/0178901 | A1* | 9/2003 | Erten | ...................... H02K 3/26 310/112 |
| 2007/0121065 | A1* | 5/2007 | Cox | ...................... A61B 3/113 351/209 |
| 2011/0066239 | A1* | 3/2011 | Smoot | ...................... A61F 2/141 623/6.64 |

FOREIGN PATENT DOCUMENTS

| CN | 1891141 A | 1/2007 |
| CN | 101137892 A | 3/2008 |
| SU | 713561 A1 | 2/1980 |

OTHER PUBLICATIONS

International Search Report of PCT Patent Application No. PCT/CN2014/088183 dated Jan. 14, 2015.
(Continued)

*Primary Examiner* — Mustak Choudhury

(57) ABSTRACT

The present invention discloses an eye motion sensing method, a flexible contact body, an external sensing coil, and a system. The method may include: sensing an eye motion by using a servo motion signal of a permanent magnet implanted into a flexible contact body; applying at least four coils disposed externally on a same plane, and monitoring a servo motion of the permanent magnet according to an electromotive force in the coils; and converting the electromotive force to restore an eye motion signal. The present invention can use the sensing coils distributed around an eyepit to detect the electromotive force generated when the eye motion leads to the servo motion of the flexible contact body, and analyze the electromotive force. Accordingly, the eye motion triggered by a perceptual task can be analyzed objectively.

12 Claims, 4 Drawing Sheets

(51) Int. Cl.
*G01D 5/14* (2006.01)
*G01D 5/20* (2006.01)
*A61B 3/00* (2006.01)
*A61B 5/11* (2006.01)
*A61B 5/00* (2006.01)

(52) U.S. Cl.
CPC .......... *A61B 5/1126* (2013.01); *A61B 5/4863* (2013.01); *A61B 5/6821* (2013.01); *G01D 5/145* (2013.01); *G01D 5/2046* (2013.01); *A61B 2562/0223* (2013.01)

(58) Field of Classification Search
CPC .... A61B 5/4863; A61B 5/6821; G01D 5/145; G01D 5/2046; A61N 1/0543; A61N 1/36046; A61N 1/3787; A61N 1/37247; A61N 1/37241; A61N 1/37229; G06F 3/013; G09B 23/28
USPC ....... 351/209, 246, 159.02, 159.03; 310/112; 318/586.2; 335/285; 600/544, 558; 607/2
See application file for complete search history.

(56) References Cited

OTHER PUBLICATIONS

1st Office Action of counterpart Chinese Patent Application No. 201310492430.5 dated Jul. 1, 2015.

\* cited by examiner

EYE MOTION SENSING METHOD, FLEXIBLE CONTACT BODY, EXTERNAL SENSING COIL AND SYSTEM

CROSS-REFERENCE TO RELATED APPLICATIONS

The present application is a Continuation Application of PCT application No. PCT/CN2014/088183 filed on Oct. 9, 2014, which claims the benefit of Chinese Patent Application No. 201310492430.5 filed on Oct. 10, 2013, the contents of which are hereby incorporated by reference.

TECHNICAL FIELD

The present invention relates to the field of eye motion detection technologies, and in particular, to an eye motion sensing method, a flexible contact body, an external sensing coil, and a system.

BACKGROUND

In the prior art, commonly used eye motion detection manners may include an imaging sensing method and a coil sensing method. The imaging detection method uses a high-speed camera to photograph a pupil image and analyze an eye motion, and this manner involves a relatively great error. In the coil sensing method, a dual induction phenomenon may be applied, two groups of right-angled coils may be disposed, one group is excitation coils that conduct a high frequency current, and the other group is detection coils. Because the two groups intersect each other, an induced potential in the detection coils is zero. An end-to-end induction coil is disposed and attached to an eyeball. If an eye motion occurs, the induction coil induces a high frequency current. A high frequency magnetic field generated by the induction current is further induced into the detection coils, so as to detect the eye motion. However, such a secondary induction phenomenon is relatively weak, the measurement precision is relatively low, and the anti-interference capability is relatively low.

SUMMARY

A main objective of the present invention is to provide an eye motion sensing method and enhance accuracy and stability of eye motion detection.

The present invention provides an eye motion sensing method, including:

sensing an eye motion by using a servo motion signal of a permanent magnet implanted into a flexible contact body, where the servo motion signal is caused by the eye motion, and the permanent magnet is distributed around a corresponding pupil area of the flexible contact body;

applying at least four coils disposed externally on a same plane, and monitoring a servo motion of the permanent magnet according to an electromotive force in the coils, where center lines of the four coils are respectively located in four directions of a plane coordinate axis, and two coils on a same axis have opposite winding directions and are serially connected; and converting the electromotive force to restore an eye motion signal.

a magnetic field direction of an induced magnetic field is consistent with a cornea plane, and a coil plane is vertical to the magnetic field direction.

Preferably, the converting includes: performing a conversion operation on the electromotive force by using a trigonometric function, and then performing compensation.

Preferably, the method further includes:

storing the restored eye motion signal and uploading the eye motion signal to a data server.

The present invention further provides a flexible contact body, which collaborates with external sensing coils to sense an eye motion, where the flexible contact body contacts an eye, a permanent magnet is implanted in the flexible contact body, and the permanent magnet is distributed around a corresponding pupil area of the flexible contact body to generate an induced magnetic field that, by means of an eye motion, makes the permanent magnet generate a servo motion signal.

Preferably, a magnetic field direction of an induced magnetic field is consistent with a cornea plane.

The present invention further provides an external sensing coil, which collaborates with a flexible contact body to sense an eye motion, where the external sensing coil includes at least four coils on a same plane, and monitors a servo motion of a permanent magnet according to an electromotive force in the coils, center lines of the four coils are respectively located in four directions of a plane coordinate axis, and two coils on a same axis have opposite winding directions and are serially connected.

Preferably, a coil plane is vertical to the magnetic field direction

The present invention further provides an eye motion sensing system, including:

an induced magnetic field, configured to sense an eye motion by using a servo motion signal of a permanent magnet implanted into a flexible contact body, where the servo motion signal is caused by the eye motion, and the permanent magnet is distributed around a corresponding pupil area of the flexible contact body;

a sensing coil, configured to: apply at least four coils disposed externally on a same plane, and monitor a servo motion of the permanent magnet according to an electromotive force in the coils, where center lines of the four coils are respectively located in four directions of a plane coordinate axis, and two coils on a same axis have opposite winding directions and are serially connected; and a conversion and restoration device, configured to convert the electromotive force to restore an eye motion signal.

Preferably, a magnetic field direction of an induced magnetic field is consistent with a cornea plane, and a coil plane is vertical to the cornea plane.

Preferably, the converting includes: performing a conversion operation on the electromotive force by using a trigonometric function, and then performing compensation.

Preferably, the system further includes:

a storage and uploading device, configured to store the restored eye motion signal and upload the eye motion signal to a data server.

The present invention can use the sensing coils distributed around an eyepit to detect the electromotive force generated when the eye motion leads to the servo motion of the flexible contact body, and analyze the electromotive force. Accordingly, actions such as tiny saccades, winking and/or nystagmus triggered by a perceptual task can be analyzed objectively. In this way, important information such as brain behavior patterns and explicit changes caused by defects or training can be further analyzed.

The objective fulfillment, functional characteristics, and advantages of the present invention are hereinafter further described with reference to embodiments and accompanying drawings.

DESCRIPTION OF EMBODIMENTS

It should be understood that the specific embodiments described herein are merely used to explain the present invention but are not intended to limit the present invention.

Figure 1:
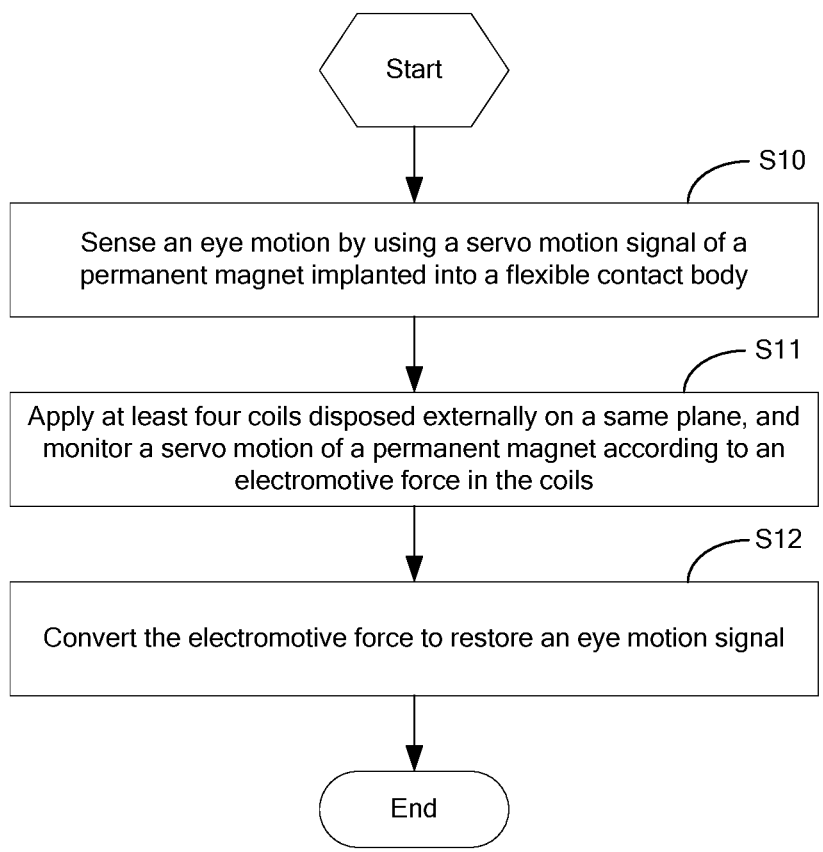
FIG. 1 is a schematic flowchart of steps in an embodiment of an eye motion sensing method according to the present invention.

Referring to FIG. 1, an embodiment of an eye motion sensing method according to the present invention is provided. The eye motion sensing method may include:

Step S10: Sense an eye motion by using a servo motion signal of a permanent magnet implanted into a flexible contact body, where the servo motion signal is caused by the eye motion, and the permanent magnet is distributed around a corresponding pupil area of the flexible contact body.

Step S11: Apply at least four coils disposed externally on a same plane, and monitor a servo motion of the permanent magnet according to an electromotive force in the coils, where center lines of the four coils are respectively located in four directions of a plane coordinate axis, and two coils on a same axis have opposite winding directions and are serially connected.

Step S12: Convert the electromotive force to restore an eye motion signal.

According to the eye motion sensing method, an annular permanent magnet of high magnetism may be implanted in the flexible contact body to form an induced magnetic field. If the magnetism of the permanent magnet is higher, it is easier to acquire the signal. The specific magnetism may be determined according to requirements. The permanent magnet is distributed around a corresponding pupil area of the flexible contact body, and does not hinder the line of sight of a testee. In this embodiment, the flexible contact body may be an eye contact device such as contact lenses. The annular permanent magnet may form an induced magnetic field, and a magnetic field direction generated by the induced magnetic field may be consistent with a cornea plane. When an eye motion occurs after the flexible contact body contacts an eye, the permanent magnet (induced magnetic field) generates a servo motion.

Then the induced magnetic field is monitored by using the sensing coil, and the servo motion generated by the induced magnetic field when the eye motion occurs is captured according to the electromotive force induced by the servo motion of the induced magnetic field. In this embodiment, the sensing coil may be disposed on a frame of worn glasses or on another bracket that is fixed around the eyepit. The sensing coil may include at least four coils on the same plane. Center lines of the four coils are on located in four directions of the plane coordinate axis respectively. The center lines may be extended to form a cross, and the four coils are located in four directions of the cross respectively.

In addition, two coils located on the same coordinate axis have opposite winding directions and are serially connected, and are conducive to eliminating outside electromagnetic interference and can induce the electromotive force generated by the servo action of the permanent magnet in the middle part of the two coils. The magnetic field direction of the induced magnetic field may be consistent with a cornea plane, and the coil plane may be vertical to the magnetic field direction.

The electromotive force induced by two groups of coils that are vertical to each other to form a cross (each group of coils are two serially connected coils that have the same direction or opposite winding directions) is converted by a trigonometric function, and the eye motion signal can be restored by making appropriate compensation. The electromotive force may include information such as strength and direction, and the eye motion signal may include information such as speed and direction.

The direction and speed of the eye motion can be calculated by means of vector summing according to the percentage and direction of the strength of the induced electromotive force. Regarding the direction and speed of the eye motion: for example, if the strength of the X axis coil is +1.5 and the Y axis strength is −1.5, the angle of the eye motion is: a=arctan (1.5/1.5)=315 (−45° refers to 360−45°, that is, 315°), which falls in the $4^{th}$ quadrant; and the speed is: S=extracting a root of the square of the strength of the two axes, that is, $S=\sqrt{1.5^2+1.5^2}=2.12$. The symbol of the X axis decides the motion toward two sides of the Y axis. That is, when the data on the X axis is positive, the direction of the motion is along the X axis arrow direction; conversely, the direction of the motion is opposite the X axis arrow direction. Similarly, when the value on the Y axis is positive, it indicates that the eyeball moves upward; conversely, it indicates that the eyeball moves downward. Therefore, the angle calculation can be simplified, and is to calculate the arctangent function of two values. The direction of the motion can be determined according to the symbols of the two values, and then a root of the square is extracted to express the speed.

Figure 2:
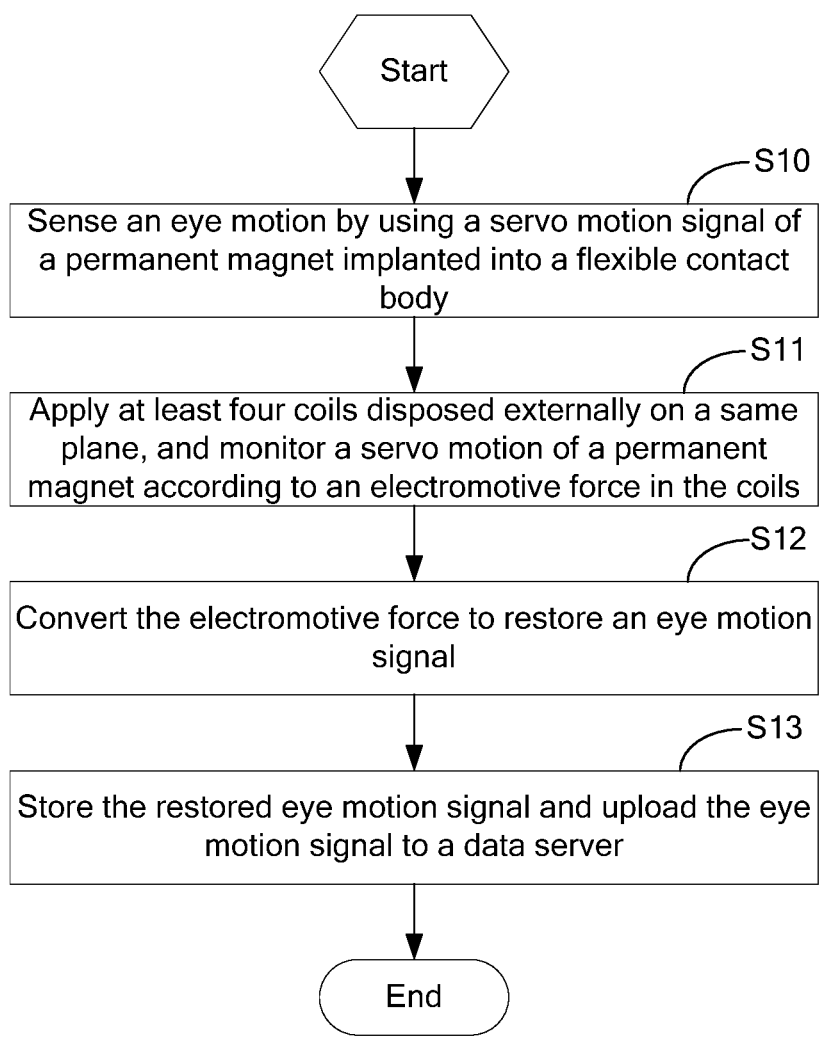
FIG. 2 is a schematic flowchart of steps in another embodiment of an eye motion sensing method according to the present invention.

Referring to FIG. 2, in another embodiment of the present invention, the eye motion sensing method may further include:

Step S13. Store the restored eye motion signal and upload the eye motion signal to a data server.

The storage and transmission of the eye motion signal may be implemented by a microcontroller, a memory, a communications device, and the like. The transmission technology may include wired transmission and wireless transmission, and may also include short distance transmission and long distance transmission. Therefore, the eye motion signal closely related to a perception task can be stored and uploaded, where the eye motion signal may include detailed information of tiny saccades, nystagmus and/or winking and the like.

According to the eye motion sensing method, a testee who wears a flexible contact body that has special magnetic field distribution performs a specific perception task, for example, a task that needs participation of attention, memory, and perception. By using the sensing coils distributed around an eyepit, the electromotive force generated when the eye motion leads to the servo motion of the flexible contact body is detected and analyzed. Accordingly, actions such as tiny saccades, winking and/or nystagmus triggered by the perceptual task can be analyzed objectively. In this way, important information such as brain behavior patterns and explicit changes caused by defects or training can be further analyzed.

Figure 3:
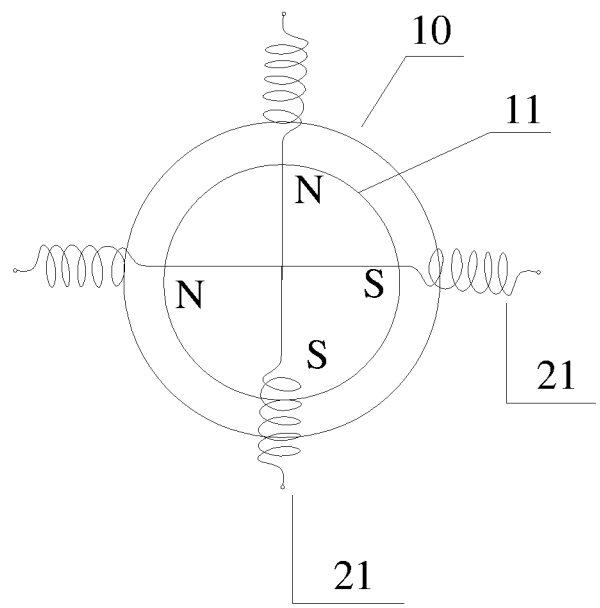
FIG. 3 is a schematic diagram of a combination of a flexible contact body and an external sensing coil in an embodiment of the present invention.

Referring to FIG. 3, an embodiment of a flexible contact body according to the present invention is provided. The flexible contact body 10 may collaborate with external sensing coils to sense an eye motion, where the flexible contact body 10 contacts an eye, a permanent magnet 11 is implanted in the flexible contact body, and the permanent magnet 11 is distributed around a corresponding pupil area of the flexible contact body 10 to generate an induced magnetic field that, by means of an eye motion, makes the permanent magnet 11 generate a servo motion signal.

In this embodiment, an annular permanent magnet 11 of high magnetism may be implanted in the flexible contact body 10 to form an induced magnetic field. If the magnetism of the permanent magnet 11 is higher, it is easier to acquire the signal. The specific magnetism may be determined according to requirements. The permanent magnet 11 is distributed around a corresponding pupil area of the flexible contact body 10, and does not hinder the line of sight of a testee. In this embodiment, the flexible contact body 10 may be an eye contact device such as contact lenses. The annular permanent magnet 11 may form an induced magnetic field, and a magnetic field direction generated by the induced magnetic field may be consistent with a cornea plane. When an eye motion occurs after the flexible contact body 10 contacts an eye, the permanent magnet (induced magnetic field) generates a servo motion.

Then the induced magnetic field is monitored by using the sensing coil, and the servo motion generated by the induced magnetic field when the eye motion occurs is captured according to the electromotive force induced by the servo motion of the induced magnetic field. In this embodiment, the sensing coil may be disposed on a frame of worn glasses or on another bracket that is fixed around the eyepit. The sensing coil may include at least four coils 21 on the same plane. Center lines of the four coils 21 are on located in four directions of the plane coordinate axis respectively. The center lines may be extended to form a cross, and the four coils 21 are located in four directions of the cross respectively. In addition, two coils 21 located on the same coordinate axis have opposite winding directions and are serially connected, and are conducive to eliminating outside electromagnetic interference and can induce the electromotive force generated by the servo action of the permanent magnet 11 in the middle part of the two coils 21. The magnetic field direction of the induced magnetic field may be consistent with a cornea plane, and the coil 21 plane may be vertical to the magnetic field direction.

The electromotive force induced by two groups of coils 21 that are vertical to each other to form a cross (each group of coils 21 are two serially connected coils 21 that have the same direction or opposite winding directions) is converted by a trigonometric function, and the eye motion signal can be restored by making appropriate compensation. The electromotive force may include information such as strength and direction, and the eye motion signal may include information such as speed and direction.

The direction and speed of the eye motion can be calculated by means of vector summing according to the percentage and direction of the strength of the induced electromotive force. Regarding the direction and speed of the eye motion: for example, if the strength of the X axis coil 21 is +1.5 and the Y axis strength is −1.5, the angle of the eye motion is: a=arctan (1.5/1.5)=315 (−45° refers to 360−45°, that is, 315°), which falls in the $4^{th}$ quadrant; and the speed is: S=extracting a root of the square of the strength of the two axes, that is, $S=\sqrt{1.5^2+1.5^2}=2.12$. The symbol of the X axis decides the motion toward two sides of the Y axis. That is, when the data on the X axis is positive, the direction of the motion is along the X axis arrow direction; conversely, the direction of the motion is opposite the X axis arrow direction. Similarly, when the value on the Y axis is positive, it indicates that the eyeball moves upward; conversely, it indicates that the eyeball moves downward. Therefore, the angle calculation can be simplified, and is to calculate the arctangent function of two values. The direction of the motion can be determined according to the symbols of the two values, and then a root of the square is extracted to express the speed.

Referring to FIG. 3, an embodiment of an external sensing coil according to the present invention is provided. The external sensing coil may collaborate with a flexible contact body 10 to sense an eye motion, where the external sensing coil includes at least four coils 21 on a same plane, and monitors a servo motion of a permanent magnet 11 according to an electromotive force in the coils 21, center lines of the four coils 21 are respectively located in four directions of a plane coordinate axis, and two coils 21 on a same axis have opposite winding directions and are serially connected.

In this embodiment, an annular permanent magnet 11 of high magnetism may be implanted in the flexible contact body 10 to form an induced magnetic field. If the magnetism of the permanent magnet 11 is higher, it is easier to acquire the signal. The specific magnetism may be determined according to requirements. The permanent magnet 11 is distributed around a corresponding pupil area of the flexible contact body 10, and does not hinder the line of sight of a testee. In this embodiment, the flexible contact body 10 may be an eye contact device such as contact lenses. The annular permanent magnet 11 may form an induced magnetic field, and a magnetic field direction generated by the induced magnetic field may be consistent with a cornea plane. When an eye motion occurs after the flexible contact body 10 contacts an eye, the permanent magnet (induced magnetic field) generates a servo motion.

Then the induced magnetic field is monitored by using the sensing coil, and the servo motion generated by the induced magnetic field when the eye motion occurs is captured according to the electromotive force induced by the servo motion of the induced magnetic field. In this embodiment, the sensing coil may be disposed on a frame of worn glasses or on another bracket that is fixed around the eyepit. The sensing coil may include at least four coils 21 on the same plane. Center lines of the four coils 21 are on located in four directions of the plane coordinate axis respectively. The center lines may be extended to form a cross, and the four coils 21 are located in four directions of the cross respectively. In addition, two coils 21 located on the same coordinate axis have opposite winding directions and are serially connected, and are conducive to eliminating outside electromagnetic interference and can induce the electromotive force generated by the servo action of the permanent magnet 11 in the middle part of the two coils 21. The magnetic field direction of the induced magnetic field may be consistent with a cornea plane, and the coil 21 plane may be vertical to the magnetic field direction.

The electromotive force induced by two groups of coils 21 that are vertical to each other to form a cross (each group of coils 21 are two serially connected coils 21 that have the same direction or opposite winding directions) is converted by a trigonometric function, and the eye motion signal can be restored by making appropriate compensation. The electromotive force may include information such as strength and direction, and the eye motion signal may include information such as speed and direction.

Figure 4:
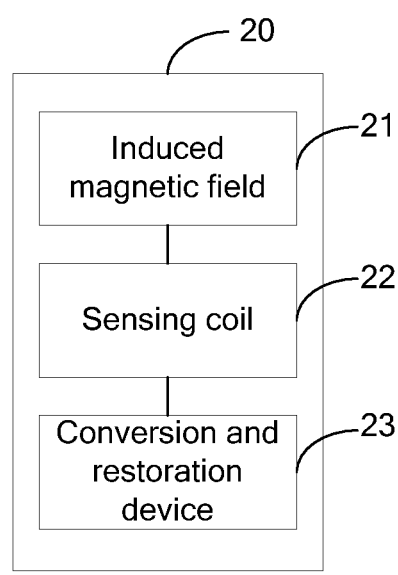
FIG. 4 is a schematic diagram of functional modules in an embodiment of an eye motion sensing system according to the present invention.

Referring to FIG. 4, an embodiment of an eye motion sensing system 30 according to the present invention is provided. The eye motion sensing system 30 may include: an induced magnetic field 31, a sensing coil 32, and a conversion and restoration device 33. The induced magnetic field 31 senses an eye motion by using a servo motion signal of a permanent magnet 11 implanted into a flexible contact body 10, where the servo motion signal is caused by the eye motion, and the permanent magnet 11 is distributed around a corresponding pupil area of the flexible contact body 10; the sensing coil 32 applies at least four coils 21 disposed externally on a same plane, and monitors a servo motion of the permanent magnet 11 according to an electromotive force in the coils 21, where center lines of the four coils 21 are respectively located in four directions of a plane coordinate axis, and two coils 21 on a same axis have opposite winding directions and are serially connected; and the conversion and restoration device 33 converts the electromotive force to restore an eye motion signal.

According to the eye motion sensing system, an annular permanent magnet 11 of high magnetism may be implanted in the flexible contact body 10 to form an induced magnetic field. If the magnetism of the permanent magnet 11 is higher, it is easier to acquire the signal. The specific magnetism may be determined according to requirements. The permanent magnet 11 is distributed around a corresponding pupil area of the flexible contact body 10, and does not hinder the line of sight of a testee. In this embodiment, the flexible contact body 10 may be an eye contact device such as contact lenses. The annular permanent magnet 11 may form an induced magnetic field 31, and a magnetic field direction generated by the induced magnetic field may be consistent with a cornea plane. When an eye motion occurs after the flexible contact body 10 contacts an eye, the permanent magnet 11 (induced magnetic field 31) generates a servo motion.

Then the induced magnetic field 31 is monitored by using the sensing coil, and the servo motion generated by the induced magnetic field 31 when the eye motion occurs is captured according to the electromotive force induced by the servo motion of the induced magnetic field 31. In this embodiment, the sensing coil 32 may be disposed on a frame of worn glasses or on another bracket that is fixed around the eyepit. The sensing coil 32 may include at least four coils 21 on the same plane. Center lines of the four coils 21 are on located in four directions of the plane coordinate axis respectively. The center lines may be extended to form a cross, and the four coils 21 are located in four directions of the cross respectively. In addition, two coils 21 located on the same coordinate axis have opposite winding directions and are serially connected, and are conducive to eliminating outside electromagnetic interference and can induce the electromotive force generated by the servo action of the permanent magnet 11 in the middle part of the two coils 21. The magnetic field direction of the induced magnetic field 31 may be consistent with a cornea plane, and the coil plane may be vertical to the magnetic field direction.

The electromotive force induced by two groups of coils 21 that are vertical to each other to form a cross (each group of coils 21 are two serially connected coils 21 that have the same direction or opposite winding directions) is converted by a trigonometric function, and the eye motion signal can be restored by making appropriate compensation. The electromotive force may include information such as strength and direction, and the eye motion signal may include information such as speed and direction.

The direction and speed of the eye motion can be calculated by means of vector summing according to the percentage and direction of the strength of the induced electromotive force. Regarding the direction and speed of the eye motion: for example, if the strength of the X axis coil 21 is +1.5 and the Y axis strength is −1.5, the angle of the eye motion is: a=arctan (1.5/1.5)=315 (−45° refers to 360−45°, that is, 315°), which falls in the $4^{th}$ quadrant; and the speed is: S=extracting a root of the square of the strength of the two axes, that is, $S=\sqrt{1.5^2+1.5^2}=2.12$. The symbol of the X axis decides the motion toward two sides of the Y axis. That is, when the data on the X axis is positive, the direction of the motion is along the X axis arrow direction; conversely, the direction of the motion is opposite the X axis arrow direction. Similarly, when the value on the Y axis is positive, it indicates that the eyeball moves upward; conversely, it indicates that the eyeball moves downward. Therefore, the angle calculation can be simplified, and is to calculate the arctangent function of two values. The direction of the motion can be determined according to the symbols of the two values, and then a root of the square is extracted to express the speed.

Figure 5:
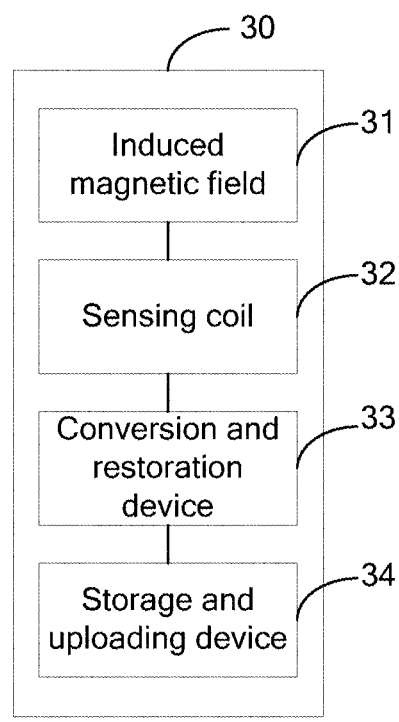
FIG. 5 is a schematic diagram of functional modules in another embodiment of an eye motion sensing system according to the present invention.

Referring to FIG. 5, in another embodiment of the present invention, the eye motion sensing system 30 may further include: a storage and uploading device 34, configured to store the restored eye motion signal and upload the eye motion signal to a data server.

The storage and transmission of the eye motion signal may be implemented by a microcontroller, a memory, a communications device, and the like. The transmission technology may include wired transmission and wireless transmission, and may also include short distance transmission and long distance transmission. Therefore, the eye motion signal closely related to a perception task can be stored and uploaded, where the eye motion signal may include detailed information of tiny saccades, nystagmus and/or winking and the like.

According to the eye motion sensing system 30, a testee who wears a flexible contact body 10 that has special magnetic field distribution performs a specific perception task, for example, a task that needs participation of attention, memory, and perception. By using the sensing coils distributed around an eyepit, the electromotive force generated when the eye motion leads to the servo motion of the flexible contact body 10 is detected and analyzed. Accordingly, actions such as tiny saccades, winking and/or nystagmus triggered by the perceptual task can be analyzed objectively. In this way, important information such as brain behavior patterns and explicit changes caused by defects or training can be further analyzed.

The foregoing descriptions are only exemplary embodiments of the present invention, and are not intended to limit the patent scope of the present invention. Any equivalent structure or equivalent process transformation made by using the specification of the present invention and content of the accompanying drawings, or used directly or indirectly in other related technical fields, shall also be covered in the patent protection scope of the present invention.

What is claimed is:
1. An eye motion sensing method, comprising:
sensing an eye motion by using a servo motion signal of an induced magnetic field formed by an annular permanent magnet implanted into a flexible contact body, with a magnetic field direction generated by the induced magnetic field, wherein the servo motion signal is caused by the eye motion, and the permanent magnet is distributed around a corresponding pupil area of the flexible contact body;

applying at least four coils disposed externally on the same plane, and monitoring a servo motion of the permanent magnet according to an electromotive force in the coils, wherein center lines of the four coils are respectively located in four directions of the plane coordinate axis and extended to form a cross, the four coils are respectively located in four directions of the cross, and two coils on the same axis have opposite winding directions and are serially connected to be conducive to eliminating outside electromagnetic interference and induce the electromotive force generated by the servo action of the permanent magnet in the middle part of the two coils; and converting the electromotive force to restore an eye motion signal; and wherein a magnetic field direction of an induced magnetic field is consistent with a cornea plane, and the plane disposed by the four coils is vertical to the magnetic field direction generated by the induced magnetic field.

2. The eye motion sensing method according to claim 1, wherein the converting comprises: performing a conversion operation on the electromotive force by using a trigonometric function, and then performing compensation.

3. The eye motion sensing method according to claim 2, wherein the method further comprises: storing the restored eye motion signal and uploading the eye motion signal to a data server.

4. The eye motion sensing method according to claim 1, wherein the method further comprises: storing the restored eye motion signal and uploading the eye motion signal to a data server.

5. The eye motion sensing method according to claim 1, wherein the method further comprises: storing the restored eye motion signal and uploading the eye motion signal to a data server.

6. A flexible contact body, which collaborates with external sensing coils to sense an eye motion by using a servo motion signal of an induced magnetic field formed by an annular permanent magnet, wherein the flexible contact body contacts an eye, the permanent magnet is implanted in the flexible contact body, with a magnetic field direction generated by the induced magnetic field, and the permanent magnet is distributed around a corresponding pupil area of the flexible contact body to generate an induced magnetic field that, by means of an eye motion, makes the permanent magnet generate the servo motion signal, wherein the external sensing coil comprises at least four coils on the same plane, and monitors the servo motion of the permanent magnet according to an electromotive force in the coils, center lines of the four coils are respectively located in four directions of the plane coordinate axis and extended to form a cross, the four coils respectively located in four directions of the cross, and two coils on the same axis have opposite winding directions and are serially connected to be conducive to eliminating outside electromagnetic interference and induce the electromotive force generated by the servo action of the permanent magnet in the middle part of the two coils and wherein the magnetic field direction generated by the induced magnetic field is consistent with a cornea plane.

7. An external sensing coil, which collaborates with a flexible contact body to sense an eye motion by using a servo motion signal of an induced magnetic field formed by an annular permanent magnet, with a magnetic field direction generated by the induced magnetic field, wherein the external sensing coil comprises at least four coils on the same plane, and monitors a servo motion of the permanent magnet according to an electromotive force in the coils, center lines of the four coils are respectively located in four directions of the plane coordinate axis and extended to form a cross, the four coils respectively located in four directions of the cross, and two coils on a same axis have opposite winding directions and are serially connected to be conducive to eliminating outside electromagnetic interference and induce the electromotive force generated by the servo action of the permanent magnet in the middle part of the two coils; and wherein the plane disposed by the four coils is vertical to the magnetic field direction generated by the induced magnetic field.

8. An eye motion sensing system, comprising:
an induced magnetic field, configured to sense an eye motion by using a servo motion signal of an induced magnetic field formed by an annular permanent magnet implanted into a flexible contact body, with a magnetic field direction generated by the induced magnetic field, wherein the servo motion signal is caused by the eye motion, and the permanent magnet is distributed around a corresponding pupil area of the flexible contact body;
a sensing coil, configured to: apply at least four coils disposed externally on the same plane, and monitor a servo motion of the permanent magnet according to an electromotive force in the coils, wherein center lines of the four coils are respectively located in four directions of the plane coordinate axis and extended to form a cross, the four coils are respectively located in four directions of the cross, and two coils on the same axis have opposite winding directions and are serially connected to be conducive to eliminating outside electromagnetic interference and induce the electromotive force generated by the servo action of the permanent magnet in the middle part of the two coils; and
a conversion and restoration device, configured to convert the electromotive force to restore an eye motion signal; and wherein the magnetic field direction generated by the induced magnetic field is consistent with a cornea plane, and the plane disposed by the four coils is vertical to the cornea plane.

9. The eye motion sensing system according to claim 8, wherein the converting comprises: performing a conversion operation on the electromotive force by using a trigonometric function, and then performing compensation.

10. The eye motion sensing system according to claim 9, wherein the system further comprises: a storage and uploading device, configured to store the restored eye motion signal and upload the eye motion signal to a data server.

11. The eye motion sensing system according to claim 8, wherein the system further comprises: a storage and uploading device, configured to store the restored eye motion signal and upload the eye motion signal to a data server.

12. The eye motion sensing system according to claim 8, wherein the system further comprises: a storage and uploading device, configured to store the restored eye motion signal and upload the eye motion signal to a data server.

* * * * *